(12) United States Patent
Omura

(10) Patent No.: US 9,707,170 B2
(45) Date of Patent: Jul. 18, 2017

(54) WATER-BASED SKIN COSMETIC

(71) Applicant: Shiseido Company, Ltd., Tokyo (JP)

(72) Inventor: Takayuki Omura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 12 days.

(21) Appl. No.: 14/358,743

(22) PCT Filed: Oct. 25, 2012

(86) PCT No.: PCT/JP2012/077546
§ 371 (c)(1),
(2) Date: May 16, 2014

(87) PCT Pub. No.: WO2013/080717
PCT Pub. Date: Jun. 6, 2013

(65) Prior Publication Data
US 2014/0323591 A1   Oct. 30, 2014

(30) Foreign Application Priority Data

Dec. 1, 2011 (JP) ................................. 2011-263488
Dec. 1, 2011 (JP) ................................. 2011-263489

(51) Int. Cl.
*A61K 8/81* (2006.01)
*A61K 8/86* (2006.01)
*A61Q 19/00* (2006.01)
*A61K 8/04* (2006.01)
*A61K 8/58* (2006.01)
*A61Q 19/02* (2006.01)
*A61Q 19/08* (2006.01)
*A61K 8/06* (2006.01)
*A61K 8/37* (2006.01)

(52) U.S. Cl.
CPC ............ *A61K 8/8158* (2013.01); *A61K 8/042* (2013.01); *A61K 8/062* (2013.01); *A61K 8/375* (2013.01); *A61K 8/585* (2013.01); *A61K 8/86* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 5,626,853 A * | 5/1997 | Bara .................... | A61K 8/042 424/401 |
| 5,736,128 A * | 4/1998 | Chaudhuri .......... | A61K 8/8147 424/78.02 |
| 5,958,387 A | 9/1999 | Bara | |
| 2005/0222001 A1 | 10/2005 | Baumeister | |
| 2008/0064761 A1 | 3/2008 | Gondek | |
| 2010/0029787 A1 | 2/2010 | Kaneda | |

FOREIGN PATENT DOCUMENTS

| | | |
|---|---|---|
| EP | 1 505 139 A1 | 2/2005 |
| JP | H07-258029 A | 10/1995 |
| JP | 2001-181609 A | 7/2001 |
| JP | 2004-043785 A | 2/2004 |
| JP | 2005-289994 A | 10/2005 |
| JP | 2005-320263 A | 11/2005 |
| JP | 2006-257021 A | 9/2006 |
| JP | 2007-531776 A | 11/2007 |
| JP | 2009-102281 A | 5/2009 |
| JP | 2009-126806 A | 6/2009 |
| JP | 2009-292734 A | 12/2009 |
| JP | 2010070534 | * 4/2010 |

OTHER PUBLICATIONS

Japan Patent Office, "Notification of Reasons for Refusal," issued in JP 2011-263488 to which PCT/JP2012/077546 claims priority, dispatched on Jan. 25, 2013.
Amendment and Remarks filed by Applicant on Mar. 5, 2013, in JP 2011-263488 to which PCT/JP2012/077546 claims priority.
Japan Patent Office, "Notification of Reasons for Refusal," issued in JP 2011-263489 to which PCT/JP2012/077546 claims priority, dispatched on Jan. 28, 2013.
Amendment and Remarks filed by Applicant on Feb. 22, 2013, in JP 2011-263489 to which PCT/JP2012/077546 claims priority.
Japan Patent Office, "Notification of Reasons for Refusal," issued in JP 2011-263489 to which PCT/JP2012/077546 claims priority, dispatched on Oct. 24, 2013.
Amendment and Remarks filed by Applicant on Nov. 21, 2013, in JP 2011-263489 to which PCT/JP2012/077546 claims priority.

(Continued)

*Primary Examiner* — Jennifer A Berrios

(57) ABSTRACT

The present invention provides a water-based skin cosmetic comprising the following ingredients (A) and (B):

(A) A compound represented by the following formula (I)

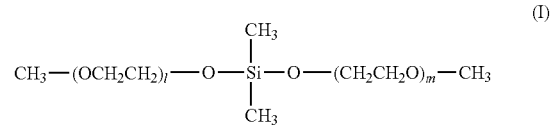

(In this formula, l and m can be either the same or different; each denotes an integer 10-25.)

(B) A thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2 methylpropane sulfonic acid under the conditions in which a single phase microemulsion or fine W/O emulsion is formed by using a surfactant.

2 Claims, No Drawings

(56) References Cited

OTHER PUBLICATIONS

The International Bureau of WIPO, "Notification of Transmittal of Translation of the International Preliminary Report on Patentability," issued in International Application No. PCT/JP2012/077546, of which U.S. Appl. No. 14/358,743 is a U.S. national phase entry, with a date of mailing of Jun. 12, 2014.

European Patent Office, "Extended European Search Report," issued in European Patent Application No. 12 852 837.9, which is a European counterpart of U.S. Appl. No. 14/358,743, with an issuance date of Jul. 14, 2015, 5 pages.

* cited by examiner

WATER-BASED SKIN COSMETIC

CROSS REFERENCE TO RELATED APPLICATIONS

This patent application is a U.S. national stage application under 35 U.S.C. §371 of International Patent Application No. PCT/JP2012/077546 filed on Oct. 25, 2012, which claims the benefit of foreign priority to Japanese Patent Application No. JP 2011-263488 filed on Dec. 1, 2011, and to Japanese Patent Application No. JP 2011-263489 filed on Dec. 1, 2011, the disclosures of all of which are hereby incorporated by reference in their entireties. The International Application was published in Japanese on Jun. 6, 2013, as International Publication No. WO 2013/080717 A1 under PCT Article 21(2).

TECHNICAL FIELD

The present invention relates to a skin cosmetic having superior texture. More specifically, it relates to a water-based skin cosmetic or oil-in-water emulsified skin cosmetic that manifests good spreadability on and absorption into the skin, is free of stickiness, and is excellent in terms of texture such as dewy freshness, permeating sensation, emollient sensation, and taut sensation.

BACKGROUND ART

Conventionally, in order to enhance moist rich sensations, smooth spreadability, and emollient sensations, skin cosmetics have been prepared by blending in polyhydric alcohols such as glycerin, 1,3-butylene glycol, and dipropylene glycol as water-based ingredients, and then solid oils including higher fatty acids such as stearic acid, palmitic acid, myristic acid, and behenic acid, waxes such as petrolatum, carnauba wax, candelilla wax, ceresin, and microcrystalline wax, and higher alcohols such as lauryl alcohol, myristyl alcohol, palmityl alcohol, stearyl alcohol, and behenyl alcohol are blended in, followed by emulsification using an emulsifying agent, to obtain an oil-in-water emulsified cosmetic.

In order to suppress crystal precipitation of these solid oils over time, attempts have been made to avoid crystal precipitation of the solid oils by adding hydrocarbon oils that are compatible with said solid oils and are liquid at ordinary temperatures such as liquid paraffin and squalane, and ester oils having relatively long carbon chains, equivalent in length to the carbon chains of the solid oils, such as cetyl palmitate, isopropyl isostearate, isodecyl pivalate, and oleyl oleate (for example, refer to Non-Patent Document 1).

However, oil-in-water emulsified skin cosmetics prepared with the method as described above, when applied on the skin, manifest emollient sensations and taut sensations but spreadability and absorption into the skin are not good, and they are sticky, resulting in an unsatisfactory usability.

On the other hand, when solid oils are not added, the products are superior in that spreadability and absorption into the skin are good and there is no stickiness, but an absence of the emollient sensation and taut sensation becomes problematic.

In recent years, skin cosmetics using homopolymers or copolymers having acrylic acid and/or acrylamide skeletons and pentaerythritol ester or dipentaerythritol ester and/or tripentaerythritol have been proposed.

However, for these skin cosmetics, even though they could give a good emollient sensation to the skin, the stickiness after the application was not sufficiently reduced (for example, see Patent Document 1).

In the field of skin cosmetics, for the purpose of improving the smoothness at the time of the application and reducing the stickiness after application, it has been known to use paste-like silicon elastomers prepared by using various liquid oil agents such as dimethicone and trioctanoin as the solvent for the following: silicone oils such as decamethylcyclopentasiloxane, dimethylpolysiloxane, methylphenylpolysiloxane, methylphenylpolysiloxane, caprylyl methicone, and methylhydrogenpolysiloxane; silicone rubbers such as high polymer dimethylpolysiloxane and amino-modified high polymer dimethylpolysiloxane; three-dimensional silicone cross-linked compounds such as (dimethicone/vinyl dimethicone) crosspolymers, (dimethicone/phenyl dimethicone) crosspolymers, (vinyl dimethicone/lauryl dimethicone) crosspolymers, (lauryl dimethicone/polyglycerin-3) crosspolymers, (lauryl polydimethylsiloxyethyl dimethicone/bis vinyl dimethicone) crosspolymers, and dimethicone crosspolymers.

However, when they were blended into oil-in-water emulsified skin cosmetics, compatibility with other oil components, such as hydrocarbon oils, ester oils, waxes, etc., in the oil phase had to be taken into account, which put constraints on formulation configurations (for example, see Patent Document 2 and Patent Document 3).

Furthermore, when oil-based ingredients such as silicones, esters, and hydrocarbons were to be blended into a water-based base agent, they needed to be emulsified, and hence an emulsifying agent was needed; this oftentimes caused an additional problem of stickiness due to the emulsifying agent.

PRIOR ART DOCUMENTS

Patent Documents

Patent Document 1: JP 2007-531776 A
Patent Document 2: JP 2009-102281 A
Patent Document 3: JP 2009-126806 A

Non-Patent Documents

Non-Patent Document 1: The Society of Cosmetic Chemists of Japan, "Saishin-Keshohin-Kagaku [Newest Cosmetic Science] (revised and enlarged II)", Yakuji Nippo Limited, Jul. 10, 1992, pp. 49.

OUTLINE OF THE INVENTION

Problem that the Present Invention Aims to Solve

The inventors conducted earnest research based on the observation that skin cosmetics prepared with the aforementioned conventional technology show poor spreadability and poor absorption on the skin, and are sticky and inferior in terms of dewy freshness, the sensation of active ingredients permeating into the skin (sensation of permeation), emollient sensation, and taut sensation, and newly discovered that, by preparing a water-based skin cosmetic by blending in a specific compound represented by the following ingredient (A) and a thickener composed of a specific microgel represented by the following ingredient (B), a water-based skin cosmetic can be obtained that manifests good spreadability on and absorption into the skin, is free of stickiness, and is excellent in terms of texture such as dewy freshness, the sensation of the active ingredients permeating into the skin (permeating sensation), emollient sensation, and taut sensation, thus completing the present invention.

(A) A compound represented by the following formula (I)

[Chemical formula 1-1]

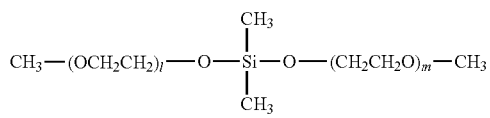
(I)

(In this formula, l and m can be either the same or different; each denotes an integer 10-25.)

(B) A thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant.

Also, the inventors considered the problem that oil-in-water emulsified skin cosmetics prepared with the aforementioned technology have poor spreadability and absorption into the skin, are sticky, and are inferior in terms of dewy freshness, the sensation of the active ingredients permeating into the skin (permeating sensation), emollient sensation, and taut sensation, and conducted earnest research and newly discovered that (C) an ester of a fatty acid mixture comprising a fatty acid having 16-18 carbon atoms and pentaerythritol, and (D) a thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant, could be blended into an oil-in-water emulsified skin cosmetic to obtain an oil-in-water emulsified skin cosmetic that manifests good spreadability on and absorption into the skin, is free of stickiness, and is excellent in terms of texture such as dewy freshness, the sensation of the active ingredients permeating into the skin (permeating sensation), emollient sensation, and taut sensation, thus completing the present invention.

The object of the present invention is to provide a water-based skin cosmetic or an oil-in-water emulsified skin cosmetic that manifests good spreadability on and absorption into the skin, is free of stickiness, and has a texture superior in terms of dewy freshness, the sensation of the active ingredients permeating into the skin (permeating sensation), emollient sensation, and taut sensation.

Means to Solve the Problem

That is, the present invention provides a water-based skin cosmetic comprising the following ingredients (A) and (B):

(A) A compound represented by the following formula (I)

[Chemical formula 1-2]

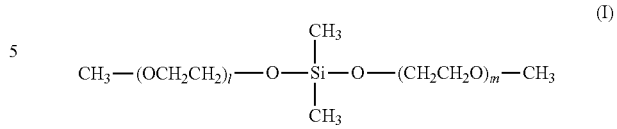
(I)

(In this formula, l and m can be either the same or different; each denotes an integer 10-25.)

(B) A thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant.

Also, the present invention provides the aforementioned water-based skin cosmetic wherein the blend ratio of the compound represented by said ingredient (A), the following formula (I), is 1.0-10.0 wt % and the blend ratio of the thickener composed of microgel of said ingredient (B) is 0.1-2.0 wt % relative to the total amount of the water-based skin cosmetic.

[Chemical formula 1-3]

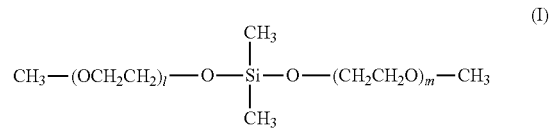
(I)

(In this formula, l and m can be either the same or different; each denotes an integer 10-25.)

That is, the present invention provides an oil-in-water emulsified skin cosmetic comprising the following ingredients (C) and (D):

(C) an ester of a fatty acid mixture comprising a fatty acid having 16-18 carbon atoms and pentaerythritol, and (D) a thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant.

Also, the present invention provides the aforementioned oil-in-water emulsified skin cosmetic wherein the blend ratio of said ingredient, (C) an ester of a fatty acid mixture comprising a fatty acid having 16-18 carbon atoms and pentaerythritol, is 0.5-5.0 wt % and the blend ratio of the thickener composed of microgel of said ingredient (D) is 0.1-2.0 wt % relative to the total amount of the oil-in-water emulsified skin cosmetic.

Effects of the Invention

The water-based skin cosmetic or an oil-in-water emulsified skin cosmetic of the present invention is a water-based skin cosmetic or an oil-in-water emulsified skin cosmetic that manifests good spreadability on and absorption into the skin, is free of stickiness, and has texture superior in terms of dewy freshness, the sensation of the active ingredients permeating into the skin (permeating sensation), emollient sensation, and taut sensation.

THE EMBODIMENTS OF THE PRESENT INVENTION

The water-based skin cosmetic of the present invention is described in detail below.

In the present invention, a water-based skin cosmetic stands for a skin cosmetic including 1) a cosmetic that contains water as an essential ingredient and does not contain an emulsifier wherein the base agent that constitutes the water based skin cosmetic is composed only of a water-based base agent, and 2) an oil-in-water emulsified skin cosmetic that contains water as the outer phase.

"(A) A compound represented by the following formula (I)"

Ingredient (A) used in the water-based skin cosmetic is a chemical compound represented by the following formula (I). In the present invention, at least one, two or more chemical compounds that satisfy the following formula (I) are blended in.

[Chemical formula 1-4]

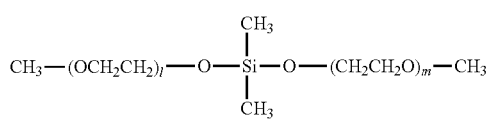

(I)

(In this formula, l and m can be either the same or different; each denotes an integer 10-25.)

The compound represented by formula (I) is paste or solid at room temperature.

Ingredient (A) shows good compatibility with water so it is a water-based base agent having superior water dispersion properties and, in the water-based skin cosmetic of the present invention, disperses homogeneously across the entire cosmetic. Therefore, it does not need an emulsifying agent, which is conventionally needed for blending silicones in a water-based base agent. Therefore, it is superior in that it can reduce stickiness which is caused by an emulsifying agent.

For commercially available products, those sold with INCI designation "bis-PEG-18 methyl ether dimethyl silane" can be used.

Specific commercially available products include "2501 Cosmetic Wax (from Dow Corning Toray Company Ltd.)" and "SM4110P (from KCC Corporation)." These are both chemical compounds having a structure in which the average of each of l and m in the aforementioned formula (I) is 18.

The blend ratio of ingredient (A) used in the present invention is preferably 1.0-10.0 wt %, more preferably 2.0-8.0 wt %, relative to the total amount of the water-based skin cosmetic.

If it is less than 1.0 wt %, then the effect of the present invention, i.e., good spreadability and good absorption into the skin at the time of use, cannot be felt. On the other hand, blending in more than 10.0 wt % does not augment the effect of the present invention and instead causes stickiness at the time of use.

"(B) A thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant"

The thickener composed of ingredient (B), microgel, used in the present invention is polymer microgel used as a thickener manufactured by the polymerization method generally called the reverse emulsion polymerization method; its polymerization method and mechanical properties are different from those of a thickener consisting of a synthetic polymer obtained by a homogeneous polymerization system disclosed in, for example, JP 2001-114641 A.

In order to blend the thickener obtained from the homogeneous polymerization system disclosed in JP 2001-114641 A into a cosmetic, it has to be pulverized into a powder form and it may cause a problem in terms of appearance due to the noticeable synthetic polymer gel.

Details of the thickener composed of ingredient (B), microgel, used in the present invention is described in JP 2004-43785 A; a thickener composed of microgel that is fine particles of a synthetic polymer electrolyte prepared with the reverse phase microemulsion polymerization method can provide a visually homogeneous highly viscous solution and therefore would not cause an appearance problem when blended into a cosmetic.

For the water soluble ethylene type unsaturated monomer that constitutes the thickener composed of microgel, joint use of a nonionic monomer and an ionic monomer (anionic monomer or cationic monomer) is preferable.

For the nonionic monomer, the dialkylacrylamide represented by the following general formula (II) is preferable.

[Chemical formula 2]

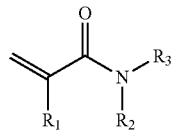

General formula (II)

($R_1$ denotes a H or methyl group; $R_2$ and $R_3$, independent of each other, denote a methyl, ethyl, propyl, or isopropyl group.)

For the "ionic monomer", the anionic acrylamide derivative represented by general formula (III) or the cationic acrylamide derivative represented by general formula (IV) is preferable.

[Chemical formula 3]

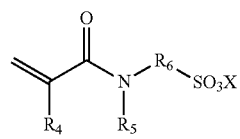

General formula (III)

($R_4$ and $R_5$, independent of each other, denote a H or methyl group, $R_6$ denotes a straight chain or branched alkyl group having 1-6 carbon atoms, and X denotes a metal ion, $NH_3$, or an amine compound. For example, the metal ion is Li, Na, or K, which are alkali metal ions, and the amine compound is triethanolamine, triisopropanoiamine, etc.)

[Chemical formula 4]

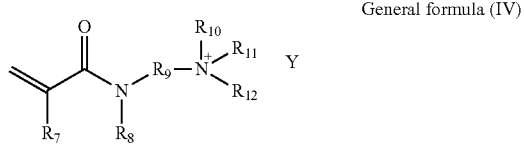

General formula (IV)

($R_7$ denotes a H or methyl group, $R_8$ denotes a H or straight chain or branched alkyl group having 1-6 carbon atoms, $R_9$ denotes a straight chain or branched alkyl group having 1-6 carbon atoms, $R_{10}$, $R_{11}$, and $R_{12}$ denote a methyl group or ethyl group, and Y denotes a negative counter ion, such as negative counter ions including Cl and Br.)

Particularly preferable dialkylacrylamides are dimethylacrylamide and diethylacrylamide.

Particularly preferable ionic acrylamide derivatives are 2-acrylamide-2-methylpropanesulfonic acid and its salts.

A particularly preferable cationic acrylamide derivative is N,N-dimethylaminopropylacrylamidemethyl chloride.

The monomer composition ratio of the nonionic monomer and the ionic monomer in the polymerization system (feed ratio of the polymerization system) is selected based on the monomer composition ratio of the target microgel. The monomer composition ratio of the microgel and the feed ratio into the polymerization system are about the same. The feed ratio of the nonionic monomer and the ionic monomer in the polymerization system (molar ratio) for copolymerization is usually in the range of Nonionic monomer:Ionic monomer=0.5:9.5 to 9.5:0.5, preferably 1:9 to 9:1, more preferably 7:3 to 9:1. The optimum ratio is Nonionic monomer:Ionic monomer=8:2.

The aforementioned water soluble ethylene type unsaturated monomer is then chosen at will and the thickener composed of microgel of the present invention is polymerized. A particularly preferable thickener is a dipolymer microgel copolymerized from monomers of dimethylacrylamide and 2-acrylamide-2-methylpropanesulfonic acid, used as the water soluble ethylene type unsaturated monomer. In this case, without requiring a cross-linking monomer, a thickener that exhibits a superior thickening effect and texture can be obtained by self cross-linking.

It is also preferable to use a cross-linking monomer; for the present invention, it is also preferable to use cross-linked N,N-dimethylacrylamide-2-acrylamide-2-methylpropanesulfonic acid sodium salt copolymer. In that case, a cross-linking monomer represented by general formula (V) is preferable, and methylenebisacrylamide is particularly preferable.

[Chemical formula 5]

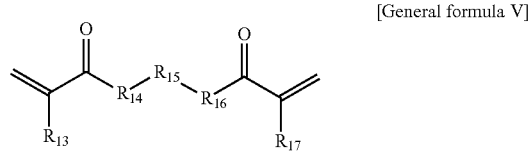

[General formula V]

{$R_{13}$ and $R_{17}$ denote H or a methyl group,
$R_{14}$ and $R_{16}$ denote —O— or —N(H)—
and $R_{15}$ denotes a straight chain or branched alkyl group having 1-6 carbon atoms
or —(CH$_2$CH$_2$O)$_n$— (where n = 4-100).}

The blend ratio of the cross-linking monomer is preferably 0.0001-2.0 mole % relative to the total moles of the 2-acrylamide-2-methylpropanesulfonic acid or its salt and the dialkylacrylamide. If it is less than 0.0001 mole %, then the obtained thickener may not exhibit the effect of cross-linking. If more than 2 mole % is used for preparation, a sufficient thickening effect may not be achieved because the cross-link density is too high and the microgel cannot swell enough.

The weight average molecular weight of the microgel used in the present invention is 100,000-5,000,000 (PEG equivalent, measured with GPC); it is adjusted according to the desired viscosity of the thickener.

The microgel that constitutes the present invention has all the rheological properties listed in (1)-(3) below. A thickener consisting of this microgel is obtained by the manufacturing method according to the aforementioned polymerization method and used preferably as a thickener.

(1) The apparent viscosity of the water dispersion having 0.5% (mass percentage) of the microgel in water is 10,000 mPa·s or higher at a shear rate of $1.0 \text{ s}^{-1}$.

(2) The apparent viscosity of the ethanol dispersion having 0.5% (mass percentage) of the microgel is 5,000 mPa·s or higher at a shear rate of $1.0 \text{ s}^{-1}$.

(3) The dynamic elastic modulus of the water or ethanol dispersion having 0.5% (mass percentage) of it satisfies the relationship G'>G" at a strain of 1% or less and a frequency range of 0.01-10 Hz.

The apparent viscosity of the ethanol or water dispersion having the microgel is the viscosity measured with a cone plate rheometer (MCR-300 from Paar Rhysica) at 25° C. and a shear rate of $1 \text{ s}^{-1}$.

The dynamic elastic modulus here refers to the stored elastic modulus (G') and the loss elastic modulus (G") measured at a strain of 1% or less and a frequency range of 0.01-10 Hz with the aforementioned measurement apparatus at a temperature of 25° C.

Following the polymerization, the microgel can be isolated in a powder form after a precipitation/purification process. The microgel thus isolated in a powder form is easily dispersed in water, ethanol, or a water/ethanol mixed solvent and quickly swells and functions as a thickener.

Also, by choosing a strongly acidic monomer (a monomer containing a sulfonic acid residue, for example) for the ionic monomer to be copolymerized into the microgel, even an acidic formulation can be thickened, which was not possible with conventional carboxyvinyl polymers.

The blend ratio of said thickener composed of the microgel used in the present invention is 0.1-2.0 wt %, preferably 0.2-1.5 wt %, relative to the total amount of the oil-in-water emulsified skin cosmetic. If the blend ratio is over 2.0 wt %, then there may be a problem in terms of stickiness or dewy freshness. On the other hand, if it is less than 0.1 wt %, then, in terms of texture, the taut sensation becomes inferior and a problem with stability may arise over time.

The oil-in-water emulsified skin cosmetic of the present invention is described in detail below.

"(C) an ester of a fatty acid mixture comprising a fatty acid having 16-18 carbon atoms and pentaerythritol"

Ingredient "(C) an ester of a fatty acid mixture comprising a fatty acid having 16-18 carbon atoms and pentaerythritol" functions as an oil component in the present invention and it is an ingredient that constitutes the oil phase of the oil-in-water emulsified skin cosmetic of the present invention.

In the present invention, in addition to the ester of a fatty acid mixture comprising a fatty acid having 16-18 carbon atoms and pentaerythritol, other oil components such as hydrocarbons, silicone oils, waxes, fatty acid esters, higher alcohols, and other oil-based ingredients can be blended in to prepare the skin cosmetic. Specific oil components that can be blended in will be described later.

The ester of a fatty acid mixture comprising a fatty acid having 16-18 carbon atoms and pentaerythritol used in the present invention retains a hydroxyl group in its structure and therefore it has a hydration function and the superior effect of giving a moisture retaining function to the skin.

In the present invention, a fatty acid mixture comprising a fatty acid having 16-18 carbon atoms means a mixture containing a large amount of the fatty acid that forms an ester with pentaerythritol and is a saturated or unsaturated fatty acid having 16-18 carbon atoms and straight chains or branched chains.

For the ester with pentaerythritol, monoesters and diesters are preferable, and even more preferable is an ester of which 75 mole % or more is diester.

For commercial products of the ester of a fatty acid mixture comprising a fatty acid having 16-18 carbon atoms and pentaerythritol, those commercially available having an INCI designation "Pentaerythrityl Distearate" can be used. Examples of commercially available product names include "Cutina PES (from Cognis GmbH)", "Dub DSPE (from Stearinerie Dubois Fils)", and "Radiasurf 7175 (from Oleon NV)".

The blend ratio of the ester of a fatty acid mixture comprising a fatty acid having 16-18 carbon atoms and pentaerythritol is preferably 0.5-5.0 wt %, more preferably 1.0-3.0 wt %, relative to the total amount of the oil-in-water emulsified skin cosmetic.

If it is less than 0.5 wt %, then the effect of the present invention, i.e., moist rich sensations at the time of use and emollient sensations after the use, cannot be felt. On the other hand, blending in more than 5.0 wt % does not augment the effect of the present invention and instead causes stickiness at the time of use.

"(D) A thickener composed of microgel obtained by using a composition that has an organic solvent or oil component as the dispersion medium and water as the dispersion phase, dissolving a water soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant"

Ingredient (D), the thickener composed of microgel, used in the present invention is the same as said ingredient (B).

In addition to the aforementioned essential ingredients, oil components, water, emulsifying agents (surfactants), humectants, and other ingredients usually used in cosmetics can be blended in as appropriate into the water-based skin cosmetic of the present invention or the oil-in-water emulsified skin cosmetic of the present invention as long as the effect of the present invention is not adversely affected, followed by mixing with a conventional method to obtain the cosmetic.

If the water-based skin cosmetic of the present invention is an oil-in-water emulsified skin cosmetic or the oil-in-water emulsified skin cosmetic of the present invention, the blend ratios of the oil component, water, and the emulsifying agent (surfactant) are determined as appropriate for the target product.

For example, if the water-based skin cosmetic of the present invention is an oil-in-water emulsified skin cosmetic or the oil-in-water emulsified skin cosmetic of the present invention, examples of the oil component constituting the oil phase include hydrocarbon oils, silicone oils, waxes, fatty acid esters, higher alcohols, and ultraviolet absorbents.

Specific examples of the hydrocarbon oils include liquid petrolatum, ozocerite, squalane, pristane, paraffin, ceresin, squalene, petrolatum, microcrystalline wax, polyethylene wax, and Fischer-Tropsch wax.

Examples of the silicone oils include chain polysiloxanes (for example, dimethylpolysiloxane, methylphenyl polysiloxane, and diphenyl polysiloxane); ring polysiloxanes (for example, decamethyl cyclopenta siloxane and dodecamethyl cyclohexa siloxane), silicone resins forming a three-dimensional network structure, silicone rubbers having an average molecular weight of 200,000 or more, and various modified polysiloxanes (amino-modified polysiloxane, polyether-modified polysiloxane, alkyl-modified polysiloxane, and fluorine-modified polysiloxane).

Examples of the waxes include honeybee wax, candelilla wax, carnauba wax, lanolin, liquid lanolin, and jojoba wax.

Examples of the fatty acid esters include myristyl myristate, cetyl palmitate, choresteryl stearate, and beeswax fatty acid 2-octyldedecyl ester.

Examples of the higher alcohols include hexyl alcohol, octyl alcohol, cetyl alcohol, stearyl alcohol, ceryl alcohol, behenyl alcohol, triacontyl alcohol, serachyl alcohol, and batyl alcohol.

Examples of the ultraviolet absorbents include the following compounds.

(1) Benzoic Acid Ultraviolet Light Absorbents

Examples include paraminobenzoic acid (hereafter abbreviated as PABA), PABA monoglycerin ester, N,N-dipropoxy PABA ethyl ester, N,N-diethoxy PABA ethyl, ester, N,N-dimethyl PABA ethyl ester, N, N-dimethyl PABA butyl ester, and N,N-dimethyl PABA ethyl ester.

(2) Anthranilic Acid Ultraviolet Light Absorbents

Examples include homo mentyl-N-acetyl anthranilate.

(3) Salicylic Acid Ultraviolet Light Absorbents

Examples include amyl salicylate, mentyl salicylate, homo mentyl salicylate, octyl salicylate, phenyl salicylate, benzyl salicylate, and p-isopropanol phenyl salicylate.

(4) Cinnamic Acid Ultraviolet Light Absorbents

Examples include octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2 ethyl hexanoyl-diparamethoxy cinnamate.

(5) Triazine Ultraviolet Light Absorbents

Examples include bisresorsinyl triazine. More specifically, bis{[4-(2-ethylhexyloxy)-2-hydroxy]phenyl}-6-(4-methoxyphenyl)-1,3,5-triazine, and 2,4,6-tris{4-(2-ethylhexyloxycarbonyl)-anilino}-1,3,5-triazine.

(6) Other Ultraviolet Light Absorbents

Examples include 3-(4'-methylbenzylidene)-d,l-camphor, 3-benzylidene-d,l-camphor, 2-phenyl-5-methyl benzoxazole, 2,2'-hydroxy-5-methylphenyl benzotriazol, 2-(2'-hydroxy-5'-t-octylphenyl)benzotriazol, 2-(2'-hydroxy-5'-methylphenyl benzotriazol, dianisoylmethane, 4-methoxy-4'-t-butyl dibenzoyl-methane, and 5-(3,3-dimethyl-2-norbornylidene)-3-pentane-2-one. Also, pyridazine derivatives such as dimorpholinopyridazinone.

The blend ratios of the ultraviolet absorbent and the oil component constituting the oil phase are determined as appropriate for the target product.

Examples of those used as a water-based base agent or the water phase ingredient of the oil-in-water emulsified skin cosmetic, along with water, include polyhydric alcohols, water soluble polymers, lower alcohols, antioxidants, preservatives, organic or inorganic acids and salts thereof, various water soluble drugs, plant extracts, and pigments. The blend ratios of the water phase ingredients are determined as appropriate for the product.

Specific examples of the polyhydric alcohols include polyethylene glycol, glycerin, diglycerin, 1,3-butylene glycol, erythritol, sorbitol, xylitol, maltitol, 1,2-pentandiol, and hexylene glycol.

Examples of the water soluble polymers include carrageenan, pectin, mannan, curdlan, chondroitin sulfuric acid, starch, glycogen, gum arabic, sodium hyaluronate, traganth gum, xanthan gum, mucoitin sulfate, hydroxyethyl guar gum, carboxymethyl guar gum, guar gum, dextran, kerato sulfate, locust bean gum, succinoglucan, chitin, chitosan, carboxymethyl chitin, and agar.

Examples of the lower alcohols include ethanol.

Examples of the antioxidants include butyl hydroxy toluene, σ-tocopherol, and phytin.

Examples of the preservatives include benzoic acid, salicylic acid, sorbic acid, alkyl paraoxybenzoates, phenoxyethanol, hexachlorophene, and ε-polylysine.

Examples of the organic or inorganic acids or salts thereof include citric acid, lactic acid, and hexametaphosphoric acid.

Examples of the various water soluble drugs include salts of L-ascorbic acid and its derivatives, salts of tranexamic acid and its derivatives, salts of alkoxysalicylic acid and its derivatives, and salts of glutathione and its derivatives.

L-ascorbic acid is commonly called vitamin C; due to its strong reduction action, it has a cellular respiration action, an enzyme activation action, and collagen formation action, and it also has a melanin reduction action. Examples of the L-ascorbic acid derivatives include: L-ascorbic acid monoalkyl esters such as L-ascorbyl monostearate, L-ascorbyl monopalmitate, and L-ascorbyl monooleate; L-ascorbic acid monoesters such as L-ascorbyl monophosphate and L-ascorbyl-2-sulfate; L-ascorbic acid dialkyl esters such as L-ascorbyl distearate, L-ascorbyl dipalmitate, and L-ascorbyl dioleate; L-ascorbic acid trialkyl esters such as L-ascorbyl tristearate, L-ascorbyl tripalmitate, and L-ascorbyl trioleate; L-ascorbic acid triesters such as L-ascorbyl triphosphate; and L-ascorbyl glucoside such as L-ascorbyl-2-glucoside. In the present invention, L-ascorbic acid, L-ascorbyl phosphate, L-ascorbyl-2-sulfate, and L-ascorbyl-2-glucoside are preferably used in a salt form.

Examples of the tranexamic acid derivatives include tranexamic acid dimmers (such as trans-4-(trans-aminomethyl cyclohexanecarbonyl)aminomethyl cyclohexancarboxylic acid chloride), esters of tranexamic acid and hydroquinone (such as trans-4-(trans-aminomethyl cyclohexanecarboxylic acid 4'-hydroxyphenyl ester), esters of tranexamic acid and gentisic acid (such as 2-(trans-4-aminomethyl cyclohexylcarbonyloxy)-5-hydroxybenzoate), and amides of tranexamic acid (such as trans-4-aminomethyl cyclohexanecarboxylic acid methyl amide, trans-4-(p-methoxybenzoyl)aminomethyl cyclohexanecarboxylic acid, and trans-4-guanidinomethyl cyclohexanecarboxylic acid). In the present invention, salts of tranexamic acid or salts of tranexamic acid derivatives are preferably used.

Alkoxysalicylic acid is salicylic acid with a hydrogen atom in the third, fourth, or fifth position substituted by an alkoxy group; the alkoxy group, i.e., the substitution group, is preferably a methoxy group, ethoxy group, propoxy group, isopropoxy group, butoxy group, or isobutoxy group, and more preferably a methoxy group or ethoxy group. Specific compound names include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, and 5-propoxysalicylic acid. In the present invention, salts of alkoxysalicylic acid or its derivatives (such as esters) are preferably used.

Selection of the salt of the aforementioned drug is not limited in particular; examples include alkaline metal salts or alkaline earth metal salts such as sodium salts, potassium salts, and calcium salts, as well as ammonium salts and amino acid salts.

In addition, examples of optional ingredients that can be blended into the present invention as an oil phase ingredient or water phase ingredient include the following.

Examples of the vitamin A derivatives include vitamin A, vitamin A palmitate, and vitamin A acetate.

Examples of the vitamin B derivatives include vitamin $B_6$ hydrochloride, vitamin $B_6$ tripalmitate, vitamin $B_6$ dioctanoate, vitamin $B_2$ and its derivatives, vitamin $B_{12}$, and vitamin $B_{15}$ and its derivatives.

Examples of the vitamin E derivatives include α-tocopherol, β-tocopherol, and vitamin E acetate.

Additionally, vitamins such as vitamin D's, vitamin H, pantothenic acid, and pantethine; γ-oryzanol, allantoin, glycyrrhizic acid (salt), glycyrrhetinic acid, stearyl glycyrrhetinate, hinokitiol, bisabolol, eucalyptol, thymol, inositol; saponins such as saikosaponin, carrot saponin, gourd saponin, and soapberry saponin; various drugs such as pantothenylethyl ether, arbutin, and cepharanthine; plant extracts such as *Rumex japonicus*, *Sophora flavescens*, *Nuphar japonica*, orange, sage, yarrow, mallow, smilax, swertia, thyme, *Ligusticum acutilohum*, bitter orange peel, birch, horsetail, gourd, horse chestnut, creeping saxifrage, scutellaria root, arnica, lily, mugwort, *Paeonia lactiflora*, aloe, gardenia, and sakura leaf, and colorings such as β-carotene can be blended in.

Also, if the water-based skin cosmetic of the present invention is an oil-in-water emulsified skin cosmetic or the oil-in-water emulsified skin cosmetic of the present invention, an emulsifying agent (surfactant) commonly used in cosmetics can be used. Specific examples include the following emulsifying agents (surfactants).

Polyglycerin fatty acid esters such as hexaglyceryl monolaurate (HLB 14.5), hexaglyceryl monomyristate (HLB 11), hexaglyceryl monostearate (HLB 9.0), hexaglyceryl monooleate (HLB 9.0), decaglyceryl monomyristate (HLB 14.0), decaglyceryl monostearate (HLB 12.0), decaglyceryl monoisostearate (HLB 12.0), decaglyceryl monooleate (HLB 12.0), decaglyceryl distearate (HLB 9.5), and decaglyceryl diisostearate (HLB 10.0).

Polyoxyethylene glycerin fatty acid esters such as polyoxyethylene 5 mole-adduct (hereafter abbreviated as POE (5)) glyceryl monostearate (HLB 9.5), POE (15) glyceryl monostearate (HLB 13.5), POE (5) glyceryl monooleate (HLB 9.5), and POE (15) glyceryl monooleate (HLB 14.5).

Polyoxyethylene sorbitan fatty acid esters such as POE (20) sorbitan monococoate (HLB 16.9), POE (20) sorbitan monopalmitate (HLB 15.6), POE (20) sorbitan monostearate (HLB 14.9), POE (6) sorbitan monostearate (HLB 9.5), POE (20) sorbitan tristearate (HLB 10.5), POE (20) sorbitan monoisostearate (HLB 15.0), POE (20) sorbitan monooleate (HLB 15.0), POE (6) sorbitan monooleate (HLB 10.0), and POE (20) sorbitan trioleate (HLB 11.0).

Polyoxyethylene sorbit fatty acid esters such as POE (6) sorbit monolaurate (HLB 15.5), POE (60) sorbit tetrastearate (HLB 13.0), POE (30) sorbit tetraoleate (HLB 11.5), POE (40) sorbit tetraoleate (HLB 12.5), and POE (60) sorbit tetraoleate (HLB 14.0).

Polyoxyethylene lanolin/lanolin alcohol/beeswax derivatives such as POE (10) lanolin (HLB 12.0), POE (20) lanolin (HLB 13.0), POE (30) lanolin (HLB 15.0), POE (5) lanolin alcohol (HLB 12.5), POE (10) lanolin alcohol (HLB 15.5), POE (20) lanolin alcohol (HLB 16.0), POE (40) lanolin alcohol (HLB 17.0), and POE (20) sorbit beeswax (HLB 9.5).

Polyoxyethylene castor oils/hydrogenated oils such as POE (20) castor oil (HLB 10.5), POE (40) castor oil (HLB 12.5), POE (50) castor oil (HLB 14.0), POE (60) castor oil (HLB 14.0), POE (20) hydrogenated castor oil (HLB 10.5), POE (30) hydrogenated castor oil (HLB 11.0), POE (40) hydrogenated castor oil (HLB 13.5), POE (60) hydrogenated castor oil (HLB 14.0), POE (80) hydrogenated castor oil (HLB 16.5), POE (40) hydrogenated castor oil and POE (100) hydrogenated castor oil (HLB 16.5).

The water-based skin cosmetic of the present invention can be preferably prepared in the product form of gel or cream, such as a moisture retaining essence, anti-aging essence, whitening essence, moisture retaining cream, anti-aging cream, whitening cream, etc.

These products can be prepared with a conventional method by mixing the essential ingredients (A) and (B) of the present invention, water, and optional ingredients usually blended into cosmetics.

The oil-in-water emulsified skin cosmetic of the present invention can be preferably prepared in the product form of gel or cream, such as a moisture retaining essence, anti-aging essence, whitening essence, moisture retaining cream, anti-aging cream, whitening cream, etc.

These products can be prepared with a conventional method by mixing the essential ingredients (C) and (D) of the present invention, water, and optional ingredients usually blended into cosmetics.

EXAMPLES

Next, the present invention is described in detail below by referring to Examples. The present invention is not limited to the following Examples. Unless otherwise noted, the blend ratio is in wt %.

First, the synthesis examples of the microgel that constitutes the thickener used in the present invention are described. The microgel obtained from a synthesis example is a thickener composed of ingredient (B) of the present invention.

Synthesis Example 1

40 g of dimethylacrylamide (from Kohjin) and 9 g of 2-acrylamide-2-methylpropanesulfonic acid (from Sigma) are dissolved in 250 g of ion-exchanged water and the pH is adjusted to 7.0 with sodium hydroxide. 250 g of n-hexane, 8.2 g of polyoxyethylene (3) oleyl ether (EMALEX 503 from Nihon Emulsion), and 16.4 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C., after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 2

35 g of dimethylacrylamide (from Kohjin) and 17.5 g of 2-acrylamide-2-methylpropanesulfonic acid (from Sigma) are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 3

30 g of dimethylacrylamide (from Kohjin) and 26.7 g of 2-acrylamide-2 methylpropanesulfonic acid (from Sigma) are dissolved in 280 g of ion-exchanged water and the ph is adjusted to 7.0 with sodium hydroxide. 280 g of n-hexane, 9.4 g of polyoxyethylene (3) oleyl ether (EMALEX 503 from Nihon Emulsion), and 19 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 4

35 g of dimethylacrylamide (from Kohjin), 17.5 g of 2-acrylamide-2-methylpropanesulfonic acid (from Sigma), and 7 mg of methylenebisacrylamide are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 5

35 g of dimethylacrylamide (from Kohjin), 17.5 g of 2-acrylamide-2-methylpropanesulfonic acid (from Sigma), and 70 mg of methylenebisacrylamide are dissolved in 260 g of ion-exchanged water and the pH is adjusted to 7.0 with sodium hydroxide. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 6

35 g of dimethylacrylamide (from Kohjin) and 17.5 g of N,N-dimethylaminopropylacrylamide methyl chloride (from Kohjin) are dissolved in 260 g of ion-exchanged water. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Synthesis Example 7

35 g of dimethylacrylamide (from Kohjin), 17.5 g of N,N-dimethylaminopropylacrylamide methyl chloride (from Kohjin), and 7 mg of methylenebisacrylamide are dissolved in 260 g of ion-exchanged water. 260 g of n-hexane, 8.7 g of polyoxyethylene (3) oleyl ether (EMALEX 503 from Nihon Emulsion), and 17.6 g of polyoxyethylene (6) oleyl ether (EMALEX 506 from Nihon Emulsion) are put into a 1,000 ml three-neck flask equipped with a refluxing apparatus, mixed and dissolved, followed by $N_2$ substitution. The monomer aqueous solution is added to this three-neck flask, and the temperature is raised to 65° C.-70° C. using an oil bath as stirring is carried out in an $N_2$ atmosphere. When the system temperature reaches 65° C.-70° C. after confirming that the system has become a semitransparent microemulsion state, 2 g of ammonium persulfate is added to the polymerization system to start the polymerization. The temperature of the polymerization system is maintained at 65° C.-70° C. for three hours while stirring to obtain the microgel. After the completion of the polymerization, acetone is added to the microgel suspension to precipitate the microgel, followed by rinsing with acetone three times to remove the remaining monomers and the surfactant. The precipitate is filtered and then dried under reduced pressure to obtain the dried microgel in a white powder form.

Moisture retaining essences (cosmetics composed only of water-based base agents) that are water-based skin cosmetics of Examples 1-1 through 1-9 and Comparative examples 1-1 through 1-9 prepared from the blend ratio compositions described in Table 1 and Table 2 were prepared with a conventional method.

The obtained moisture retaining essences (samples) were evaluated for their texture (spreadability on the skin, absorption into the skin, stickiness, dewy freshness, a permeating sensation, emollient sensation, and taut sensation) based on the following test methods.

[Texture (Spreadability on the Skin)]

Spreadability on the skin was evaluated with actual use testing by a panel of ten female specialists based on the following evaluation criteria.

(Evaluation Criteria)

⊚: All 10 of them judged that spreading was light and smooth.

○: 7-9 of them judged that spreading was light and smooth.

Δ: 3-6 of them judged that spreading was light and smooth.

X: 0-2 of them judged that spreading was light and smooth.

[Texture (Absorption into the Skin)]

Absorption into the skin was evaluated with actual use testing by a panel of ten female specialists based on the following evaluation criteria.

(Evaluation Criteria)

⊚: All 10 of them judged that absorption into the skin occurred.

○: 7-9 of them judged that absorption into the skin occurred.
Δ: 3-6 of them judged that absorption into the skin occurred.
X: 0-2 of them judged that absorption into the skin occurred.
[Texture (Stickiness)]
Stickiness was evaluated with actual use testing by a panel of ten female specialists based on the following evaluation criteria.
(Evaluation Criteria)
◎: All 10 of them judged that there was no stickiness and there was a moist sensation.
○: 7-9 of them judged that there was no stickiness and there was a moist sensation.
Δ: 3-6 of them judged that there was no stickiness and there was a moist sensation.
X: 0-2 of them judged that there was no stickiness and there was a moist sensation.
[Texture (Dewy Freshness)]
Dewy freshness was evaluated with actual use testing by a panel of ten female specialists based on the following evaluation criteria.
(Evaluation Criteria)
◎: All 10 of them judged that there was dewy freshness.
○: 7-9 of them judged that there was dewy freshness.
Δ: 3-6 of them judged that there was dewy freshness.
X: 0-2 of them judged that there was dewy freshness.
[Texture (Permeating Sensation: Sensation of the Effective Ingredients Permeating into the Skin)]
The permeating sensation was evaluated with actual use testing by a panel of ten female specialists based on the following evaluation criteria.
(Evaluation Criteria)
◎: All 10 of them judged that there was a permeating sensation.
○: 7-9 of them judged that there was a permeating sensation.
Δ: 3-6 of them judged that there was a permeating sensation.
X: 0-2 of them judged that there was a permeating sensation.
[Texture (Emollient Sensation)]
The emollient sensation was evaluated with actual use testing by a panel of ten female specialists based on the following evaluation criteria.
(Evaluation Criteria)
◎: All 10 of them judged that there was an emollient sensation.
○: 7-9 of them judged that there was an emollient sensation.
Δ: 3-6 of them judged that there was an emollient sensation.
X: 0-2 of them judged that there was an emollient sensation.
[Texture (Taut Sensation)]
The taut sensation on the skin was evaluated with actual use testing by a panel of ten female specialists based on the following evaluation criteria.
(Evaluation Criteria)
◎: All 10 of them judged that there was a taut sensation on the skin.
○: 7-9 of them judged that there was a taut sensation on the skin.
Δ: 3-6 of them judged that there was a taut sensation on the skin.
X: 0-2 of them judged that there was a taut sensation on the skin.

TABLE 1

| Ingredient name | Example 1-1 | 1-2 | 1-3 | 1-4 | 1-5 | 1-6 | 1-7 | 1-8 | 1-9 |
| --- | --- | --- | --- | --- | --- | --- | --- | --- | --- |
| (1) Ion-exchanged water | Balance | Balance | Balance | Balance | Balance | Balance | Balance | Balance | Balance |
| (2) Ingredient (A) bis-PEG-18 methyl ether dimethyl silane (*1) | 1.0 | 3.0 | 5.0 | 10.0 | 10.0 | 7.0 | 8.0 | 2.0 | 1.0 |
| (3) Glycerin | 5.0 | 5.0 | 5.0 | 5.0 | 5.0 | 5.0 | 5.0 | 5.0 | 5.0 |
| (4) 1,3-butylene glycol | 5.0 | 5.0 | 5.0 | 5.0 | 5.0 | 5.0 | 5.0 | 5.0 | 5.0 |
| (5) Ingredient (B) Microgel of Synthetic example 1 | 0.1 | 0.3 | 0.5 | 1.0 | 1.5 | 2.0 | 0.3 | 1.0 | 2.0 |
| (6) Control for ingredient (B) Carbomer | — | — | — | — | — | — | — | — | — |
| (7) Control for ingredient (B) Xanthan gum | — | — | — | — | — | — | — | — | — |
| (8) Control for ingredient (B) (Sodium acrylate/sodium acryloyldimethyltaurate) copolymer (*2) | — | — | — | — | — | — | — | — | — |
| (9) Control for ingredient (B) Ammonium polyacrylate (*3) | — | — | — | — | — | — | — | — | — |
| (10) Control for ingredient (B) Polyacrylamide (*4) | — | — | — | — | — | — | — | — | — |
| (11) Polyoxyethylene hydrogenated castor oil (60 mole ethylene oxide adduct) | — | — | — | — | — | — | 0.1 | 0.1 | 0.1 |
| (12) Control for ingredient (A) Dimethyl silicone 6 mPa·s | — | — | — | — | — | — | 1.0 | — | — |
| (13) Control for ingredient (A) Dimethyl silicone 1.5 mPa·s | — | — | — | — | — | — | — | — | — |
| (14) Control for ingredient (A) Dimethyl silicone 20 mPa·s | — | — | — | — | — | — | — | — | — |
| (15) Control for ingredient (A) Isododecane | — | — | — | — | — | — | — | 1.0 | — |
| (16) Control for ingredient (A) Cetyl ethylhexanoate | — | — | — | — | — | — | — | — | 1.0 |
| (17) Control for ingredient (A) Liquid petrolatum | — | — | — | — | — | — | — | — | — |
| (18) Citric acid | 0.02 | 0.02 | 0.02 | 0.02 | 0.02 | 0.02 | 0.02 | 0.02 | 0.02 |
| (19) Sodium citrate | 0.08 | 0.08 | 0.08 | 0.08 | 0.08 | 0.08 | 0.08 | 0.08 | 0.08 |
| (20) Phenoxyethanol | 0.5 | 0.5 | 0.5 | 0.5 | 0.5 | 0.5 | 0.5 | 0.5 | 0.5 |
| (21) Ethanol | 3.0 | 3.0 | 3.0 | 3.0 | 3.0 | 3.0 | 3.0 | 3.0 | 3.0 |

TABLE 1-continued

| Ingredient name | Example |  |  |  |  |  |  |  |  |
|---|---|---|---|---|---|---|---|---|---|
| | 1-1 | 1-2 | 1-3 | 1-4 | 1-5 | 1-6 | 1-7 | 1-8 | 1-9 |
| (22) Perfume | 0.1 | 0.1 | 0.1 | 0.1 | 0.1 | 0.1 | 0.1 | 0.1 | 0.1 |
| (23) Potassium hydroxide | — | — | — | — | — | — | — | — | — |
| Spreadability on the skin | ⊚ | ⊚ | ⊚ | ⊚ | ⊚ | ⊚ | ⊚ | ⊚ | ⊚ |
| Absorption into the skin | ⊚ | ⊚ | ⊚ | ⊚ | ⊚ | ⊚ | ○ | ○ | ○ |
| Stickiness | ⊚ | ⊚ | ⊚ | ⊚ | ⊚ | ⊚ | ○ | ○ | ○ |
| Dewy freshness | ⊚ | ⊚ | ⊚ | ⊚ | ⊚ | ⊚ | ○ | ○ | ○ |
| Permeating sensation | ⊚ | ⊚ | ⊚ | ⊚ | ⊚ | ⊚ | ○ | ○ | ○ |
| Emollient sensation | ○ | ○ | ⊚ | ⊚ | ⊚ | ⊚ | ⊚ | ⊚ | ⊚ |
| Taut sensation | ⊚ | ⊚ | ⊚ | ⊚ | ⊚ | ⊚ | ○ | ○ | ○ |

(*1) Product name: 2501 Cosmetic Wax from Dow Corning Toray
(*2) Product name: SIMULGEL EG from SEPIC
(*3) Product name: SIMULGEL A from SEPIC
(*4) Product name: SEPIGEL 305 from SEPIC

TABLE 2

| Ingredient name | Comparative example |  |  |  |  |  |  |  |  |
|---|---|---|---|---|---|---|---|---|---|
| | 1-1 | 1-2 | 1-3 | 1-4 | 1-5 | 1-6 | 1-7 | 1-8 | 1-9 |
| (1) Ion-exchanged water | Balance | Balance | Balance | Balance | Balance | Balance | Balance | Balance | Balance |
| (2) Ingredient (A) bis-PEG-18 methyl ether dimethyl silane (*1) | 1.0 | 3.0 | 5.0 | 10.0 | 10.0 | 7.0 | — | 2.0 | — |
| (3) Glycerin | 5.0 | 5.0 | 5.0 | 5.0 | 5.0 | 5.0 | 5.0 | 5.0 | 5.0 |
| (4) 1,3-butylene glycol | 5.0 | 5.0 | 5.0 | 5.0 | 5.0 | 5.0 | 5.0 | 5.0 | 5.0 |
| (5) Ingredient (B) Microgel of Synthetic exampe 1 | — | — | — | — | — | — | — | — | — |
| (6) Control for ingredient (B) Carbomer | 0.1 | — | 0.05 | — | — | — | — | — | — |
| (7) Control for ingredient (B) Xanthan gum | — | 0.1 | 0.05 | — | — | — | — | — | — |
| (8) Control for ingredient (B) (Sodium acrylate/sodium acryloyldimethyltaurate) copolymer (*2) | — | — | — | 0.5 | — | — | — | 1.0 | — |
| (9) Control for ingredient (B) Ammonium polyacrylate (*3) | — | — | — | — | 0.5 | — | — | — | — |
| (10) Control for ingredient (B) Polyacrylamide (*4) | — | — | — | — | — | 1.0 | — | — | 2.0 |
| (11) Polyoxyethylene hydrogenated castor oil (60 mole ethylene oxide adduct) | — | — | — | — | — | — | 0.1 | 0.2 | 0.5 |
| (12) Control for ingredient (A) Dimethyl silicone 6 mPa·s | — | — | — | — | — | — | 1.0 | — | — |
| (13) Control for ingredient (A) Dimethyl silicone 1.5 mPa·s | — | — | — | — | — | — | 1.0 | 1.0 | — |
| (14) Control for ingredient (A) Dimethyl silicone 20 mPa·s | — | — | — | — | — | — | — | — | 1.0 |
| (15) Control for ingredient (A) Isododecane | — | — | — | — | — | — | — | 1.0 | — |
| (16) Control for ingredient (A) Cetyl ethylhexanoate | — | — | — | — | — | — | — | 1.0 | 1.0 |
| (17) Control for ingredient (A) Liquid petrolatum | — | — | — | — | — | — | — | — | 1.0 |
| (18) Citric acid | 0.02 | 0.02 | 0.02 | 0.02 | 0.02 | 0.02 | 0.02 | 0.02 | 0.02 |
| (19) Sodium citrate | 0.08 | 0.08 | 0.08 | 0.08 | 0.08 | 0.08 | 0.08 | 0.08 | 0.08 |
| (20) Phenoxyethanol | 0.5 | 0.5 | 0.5 | 0.5 | 0.5 | 0.5 | 0.5 | 0.5 | 0.5 |
| (21) Ethanol | 3.0 | 3.0 | 3.0 | 3.0 | 3.0 | 3.0 | 3.0 | 3.0 | 3.0 |
| (22) Perfume | 0.1 | 0.1 | 0.1 | 0.1 | 0.1 | 0.1 | 0.1 | 0.1 | 0.1 |
| (23) Potassium hydroxide | Appropriate amount | — | Appropriate amount | — | — | — | — | — | — |
| Spreadability on the skin | ⊚ | Δ | ○ | ○ | Δ | ○ | ○ | ○ | Δ |
| Absorption into the skin | Δ | Δ | Δ | ○ | X | ○ | Δ | Δ | ○ |
| Stickiness | Δ | X | X | X | X | Δ | Δ | X | X |
| Dewy freshness | Δ | Δ | Δ | Δ | ○ | Δ | Δ | Δ | Δ |
| Permeating sensation | Δ | X | Δ | X | ○ | Δ | Δ | Δ | X |
| Emollient sensation | X | Δ | X | ○ | ○ | ○ | Δ | ○ | ⊚ |
| Taut sensation | X | Δ | X | ○ | Δ | ○ | Δ | ○ | ○ |

(*1) Product name: 2510 Cosmetic Wax from Dow Corning Toray
(*2) Product name: SIMULGEL EG from SEPIC
(*3) Product name: SIMULGEL A from SEPIC
(*4) Product name: SEPIGEL 305 from SEPIC Examples of Table 1 and Comparative examples of Table 2 indicate that the moisture retaining essences of Examples 1-1 through 1-9 have a superior texture in all the evaluation items.

Other Examples of the water-based skin cosmetics of the present invention are shown below.

Example 1-10 Whitening Essence

| (Ingredient) | (wt %) |
| --- | --- |
| (1) Ion-exchanged water | Balance |
| (2) Sodium hexametaphosphate | 0.1 |
| (3) Sodium hyaluronate | 0.1 |
| (4) Tranexamic acid | 2.0 |
| (5) Titanium dioxide | 0.2 |
| (6) Dipropylene glycol | 3.0 |
| (7) 1,3-Butylene glycol | 2.0 |
| (8) Glycerin | 3.0 |
| (9) Ingredient (B) microgel of Synthetic example 2 | 0.2 |
| (10) Bis-PEG-18 methyl ether dimethyl silane (Product name: 2510 Cosmetic Wax from Dow Corning Toray) | 6.0 |
| (11) Ethylparaben | 0.1 |
| (12) Rosemary extract | 0.1 |
| (13) Sage extract | 0.1 |
| (14) Alkyl-modified carboxyvinyl polymer (Product name: Pemulen TR-1 from Noveon Inc.) | 0.05 |
| (15) Polyethylene glycol monostearate (POE120) | 1.0 |
| (16) Polyether-modified silicone (Product name: KF-6017P (from Shin-Etsu Chemical Co., Ltd.) | 0.1 |
| (17) Pentaerythritol distearate (Product name: Cutina PES from BASF) | 4.0 |
| (18) α-Olefin oligomer | 1.0 |
| (19) Isohexadecane | 3.0 |
| (20) Cetyl ethylhexanoate | 1.0 |
| (21) Octocrylene | 0.1 |
| (22) Perfume | Appropriate amount |

<Preparation Method>

Ingredients (15)-(22) were homogeneously mixed and dissolved at 70° C. (oil phase). Ingredients (1)-(14) were homogeneously mixed and dissolved at 70° C. (water phase). The water phase was maintained at 70° C., to which the oil phase was gradually added, followed by emulsification with a homomixer. When the emulsification was completed, the temperature was rapidly lowered down to 40° C. or lower to obtain the target whitening essence having a viscosity of 30,000 mPa·s/30° C. (BH type viscometer, rotor No. 6, 10 rpm), <Product Properties>

The same evaluation as Examples 1 through 9 was conducted on the obtained whitening essence and the results were superior (evaluation ◎) in all texture items.

Example 1-11: Whitening Cream

| (Ingredient) | (wt %) |
| --- | --- |
| (1) Ion-exchanged water | Balance |
| (2) Edetate | 0.1 |
| (3) Sodium acetylated hyaluronate | 0.1 |
| (4) Potassium 4-methoxysalicylate | 1.0 |
| (5) Silicic acid anhydride | 0.2 |
| (6) Dipropylene glycol | 2.0 |
| (7) 1,3-Butylene glycol | 3.0 |
| (8) Glycerin | 3.0 |
| (9) Microgel of Synthetic example 3 | 0.5 |
| (10) Methylparaben | 0.1 |
| (11) Ethylparaben | 0.2 |
| (12) Hawthorn extract | 0.1 |
| (13) Runpuyan extract | 0.1 |
| (14) Bis-PEG-18 methyl ether dimethyl silane (Product name: SM4110P from KCC Corporation) | 6.0 |
| (15) POE (20) behenyl ether | 1.2 |
| (16) Behenyl alcohol | 0.4 |
| (17) Stearyl alcohol | 0.2 |
| (18) Isodecyl pivalate | 2.0 |
| (19) Isododecane | 1.0 |
| (20) Pentaerythritol distearate (Product name: Dub DSPE from Stearinerie Dubois Fits) | 7.0 |
| (21) Dimethylpolysiloxane (2 mPa · s) | 2.0 |
| (22) Hydrogenated polyisobutene | 3.0 |
| (23) Perfume | Appropriate amount |

<Preparation Method>

Ingredients (15)-(23) were homogeneously mixed and dissolved at 70° C. (oil phase). Ingredients (1)-(14) were homogeneously mixed and dissolved at 70° C. (water phase). The water phase was maintained at 70° C., to which the oil phase was gradually added, followed by emulsification with a homomixer. When the emulsification was completed, the temperature was rapidly lowered down to 40° C. or lower to obtain the target whitening cream having a viscosity of 40,000 mPa·s/30° C. (BH type viscometer, rotor No. 6, 10 rpm).

<Product Properties>

The same evaluation as Examples 1 through 9 was conducted on the obtained whitening cream and the results were superior (evaluation ◎) in all texture items.

Example 1-12 Anti-Aging Essence

| (Ingredient) | (wt %) |
| --- | --- |
| (1) Ion-exchanged water | Balance |
| (2) Edetate | 0.1 |
| (3) Sodium acetylated hyaluronate | 0.1 |
| (4) Carnosine | 3.5 |
| (5) Bis-PEG-18 methyl ether dimethyl silane (Product name: 2501 Cosmetic Wax from Dow Corning Toray) | 8.0 |
| (6) Dipropylene glycol | 2.0 |
| (7) 1,3-Butylene glycol | 3.0 |
| (8) Glycerin | 5.0 |
| (9) Microgel of Synthetic example 4 | 0.15 |
| (10) Methylparaben | 0.1 |
| (11) Phenoxyethanol | 0.3 |
| (12) Hydrolyzed yeast extract | 0.1 |
| (13) Green tea extract | 0.1 |
| (14) Potassium hydroxide | Appropriate amount |
| (15) Self-emulsified glyceryl monostearate | 1.2 |
| (16) POE (30) phytosterol | 0.9 |
| (17) POE (60) hydrogenated castor oil | 0.1 |
| (18) Behenic acid | 0.5 |
| (19) Stearic acid | 0.4 |
| (20) Isononyl isononanoate | 2.0 |
| (21) Isododecane | 1.0 |
| (22) Pentaerythritol distearate (Product name: Cutina PES from BASF) | 7.0 |
| (23) Dimethylpolysiloxane (6 mPa · s) | 2.0 |
| (24) Vitamin E acetate | 0.1 |
| (25) Perfume | Appropriate amount |

<Preparation Method>

Ingredients (15)-(25) were homogeneously mixed and dissolved at 70° C. (oil phase). Ingredients (1)-(14) were homogeneously mixed and dissolved at 70° C. (water phase). The water phase was maintained at 70° C., to which the oil phase was gradually added, followed by emulsification with a homomixer. When the emulsification was completed, the temperature was rapidly lowered down to 40° C. or lower to obtain the target whitening cream having a viscosity of 35,000 mPa·s (BE type viscometer, rotor No. 6, 10 rpm).

<Product Properties>

The same evaluation as Examples 1 through 9 was conducted on the obtained anti-aging essence and the results were superior (evaluation ⊚) in all texture items.

Moisture retaining essences (oil-in-water emulsified skin cosmetic) of Examples 2-1 through 2-9 and Comparative examples 2-1 through 2-9 composed of the blend ratio compositions described in Table 3 and Table 4 were prepared with a conventional method.

The obtained moisture retaining essences (samples) were evaluated for the texture (spreadability on the skin, absorption into the skin, stickiness, dewy freshness, a permeating sensation, emollient sensation, and taut sensation) based on the following test methods.

[Texture (Spreadability on the Skin)]

Spreadability on the skin was evaluated with actual use testing by a panel of ten female specialists based on the following evaluation criteria.
(Evaluation Criteria)
⊚: All 10 of them judged that spreading was light and smooth.
○: 7-9 of them judged that spreading was light and smooth.
Δ: 3-6 of them judged that spreading was light and smooth.
X: 0-2 of them judged that spreading was light and smooth.

[Texture (Absorption into the Skin)]

Absorption into the skin was evaluated with actual use testing by a panel of ten female specialists based on the following evaluation criteria.
(Evaluation Criteria)
⊚: All 10 of them judged that absorption into the skin occurred.
○: 7-9 of them judged that absorption into the skin occurred.
Δ: 3-6 of them judged that absorption into the skin occurred.
X: 0-2 of them judged that absorption into the skin occurred.

[Texture (Stickiness)]

Stickiness was evaluated with actual use testing by a panel of ten female specialists based on the following evaluation criteria.
(Evaluation Criteria)
⊚: All 10 of them judged that there was no stickiness and there was a moist sensation.
○: 7-9 of them judged that there was no stickiness and there was a moist sensation.
Δ: 3-6 of them judged that there was no stickiness and there was a moist sensation.
X: 0-2 of them judged that there was no stickiness and there was a moist sensation.

[Texture (Dewy Freshness)]

Dewy freshness was evaluated with actual use testing by a panel of ten female specialists based on the following evaluation criteria.
(Evaluation Criteria)
⊚: All 10 of them judged that there was dewy freshness.
○: 7-9 of them judged that there was dewy freshness.
Δ: 3-6 of them judged that there was dewy freshness.
X: 0-2 of them judged that there was dewy freshness.

[Texture (Permeating Sensation: Sensation of the Effective Ingredients Permeating into the Skin)]

The permeating sensation was evaluated with actual use testing by a panel of ten female specialists based on the following evaluation criteria.
(Evaluation Criteria)
⊚: All 10 of them judged that there was a permeating sensation.
○: 7-9 of them judged that there was a permeating sensation.
Δ: 3-6 of them judged that there was a permeating sensation.
X: 0-2 of them judged that there was a permeating sensation.

[Texture (Emollient Sensation)]

The emollient sensation was evaluated with actual use testing by a panel of ten female specialists based on the following evaluation criteria.
(Evaluation Criteria)
⊚: All 10 of them judged that there was an emollient sensation.
○: 7-9 of them judged that there was an emollient sensation.
Δ: 3-6 of them judged that there was an emollient sensation.
X: 0-2 of them judged that there was an emollient sensation.

[Texture (Taut Sensation)]

The taut sensation on the skin was evaluated with actual use testing by a panel of ten female specialists based on the following evaluation criteria.
(Evaluation Criteria)
⊚: All 10 of them judged that there was a taut sensation on the skin.
○: 7-9 of them judged that there was a taut sensation on the skin.
Δ: 3-6 of them judged that there was a taut sensation on the skin.
X: 0-2 of them judged that there was a taut sensation on the skin.

TABLE 3

| Ingredient name | Example | | | | | | | | |
| --- | --- | --- | --- | --- | --- | --- | --- | --- | --- |
|  | 2-1 | 2-2 | 2-3 | 2-4 | 2-5 | 2-6 | 2-7 | 2-8 | 2-9 |
| (1) Ion-exchanged water | Balance | Balance | Balance | Balance | Balance | Balance | Balance | Balance | Balance |
| (2) Ingredient (C) Pentaerythritol distearate (*1) | 0.5 | 1.0 | 2.0 | 3.5 | 5.0 | 4.0 | 3.0 | 2.5 | 0.5 |
| (3) Control for ingredient (C) Glycerol tri-(caprylate-caprate) | — | — | — | — | — | — | — | — | — |
| (4) Control for ingredient (C) Di-(phytostearyl/octyldodecyl-N-lauroyl-L-glutamate) (*2) | — | — | — | — | — | — | — | — | — |
| (5) Control for ingredient (C) Pentaerythrityl tetra-(behenate/benzoate/ethylhexanoate) (*3) | — | — | — | — | — | — | — | — | — |
| (6) Ingredient (D) Microgel of Synthetic example 1 | 0.1 | 0.3 | 0.5 | 1.0 | 1.5 | 2.0 | 0.3 | 1.0 | 2.0 |

TABLE 3-continued

| Ingredient name | Example 2-1 | 2-2 | 2-3 | 2-4 | 2-5 | 2-6 | 2-7 | 2-8 | 2-9 |
|---|---|---|---|---|---|---|---|---|---|
| (7) Control for ingredient (D) Carbomer | — | — | — | — | — | — | — | — | — |
| (8) Control for ingredient (D) Xanthan gum | — | — | — | — | — | — | — | — | — |
| (9) Control for ingredient (D) (Sodium acrylate/sodium acryloyldimethyltaurate) copolymer (*4) | — | — | — | — | — | — | — | — | — |
| (10) Control for ingredient (D) Ammonium polyacrylate (*5) | — | — | — | — | — | — | — | — | — |
| (11) Control for ingredient (D) Polyacrylamide (*6) | — | — | — | — | — | — | — | — | — |
| (12) Polyoxyethylene hydrogenated castor oil (60 mole ethylene oxide adduct) | 0.2 | 0.2 | 0.2 | 0.2 | 0.2 | 0.2 | 0.2 | 0.2 | 0.2 |
| (13) Dimethyl silicone 6 mPa · s | 1.0 | 1.0 | 1.0 | 1.0 | 1.0 | 1.0 | 1.0 | 1.0 | 1.0 |
| (14) Cetyl ethylhexanoate | 1.0 | 1.0 | 1.0 | 1.0 | 1.0 | 1.0 | 1.0 | 1.0 | 1.0 |
| (15) Squalane | 1.0 | 1.0 | 1.0 | 1.0 | 1.0 | 1.0 | 1.0 | 1.0 | 1.0 |
| (16) Citric acid | 0.02 | 0.02 | 0.02 | 0.02 | 0.02 | 0.02 | 0.02 | 0.02 | 0.02 |
| (17) Sodium citrate | 0.08 | 0.08 | 0.08 | 0.08 | 0.08 | 0.08 | 0.08 | 0.08 | 0.08 |
| (18) Phenoxyethanol | 0.5 | 0.5 | 0.5 | 0.5 | 0.5 | 0.5 | 0.5 | 0.5 | 0.5 |
| (19) Ethanol | 3.0 | 3.0 | 3.0 | 3.0 | 3.0 | 3.0 | 3.0 | 3.0 | 3.0 |
| (20) Perfume | 0.1 | 0.1 | 0.1 | 0.1 | 0.1 | 0.1 | 0.1 | 0.1 | 0.1 |
| (21) Potassium hydroxide | — | — | — | — | — | — | — | — | — |
| Spreadability on the skin | ◉ | ◉ | ◉ | ◉ | ◉ | ◯ | ◉ | ◉ | ◯ |
| Absorption into the skin | ◉ | ◉ | ◉ | ◉ | ◯ | ◯ | ◯ | ◯ | ◯ |
| Stickiness | ◉ | ◉ | ◉ | ◯ | ◯ | ◯ | ◯ | ◯ | ◯ |
| Dewy freshness | ◉ | ◉ | ◉ | ◉ | ◯ | ◯ | ◯ | ◉ | ◯ |
| Permeating sensation | ◉ | ◉ | ◉ | ◉ | ◉ | ◯ | ◯ | ◯ | ◯ |
| Emollient sensation | ◯ | ◯ | ◉ | ◉ | ◉ | ◉ | ◉ | ◉ | ◯ |
| Taut sensation | ◯ | ◯ | ◉ | ◉ | ◉ | ◉ | ◉ | ◯ | ◯ |

(*1) Product name: Cutina PES from BASF
(*2) Product name: Eldew PS-203 from Ajinomoto Healthy Supply
(*3) Product name: Eldew PS-304 from Ajinomoto Healthy Supply
(*4) Product name: SIMULGEL EG from SEPIC
(*5) Product name: SIMULGEL A from SEPIC
(*6) Product name: SEPIGEL 305 from SEPIC

TABLE 4

| Ingredient name | Comparative example 2-1 | 2-2 | 2-3 | 2-4 | 2-5 | 2-6 | 2-7 | 2-8 | 2-9 |
|---|---|---|---|---|---|---|---|---|---|
| (1) Ion-exchanged water | Balance | Balance | Balance | Balance | Balance | Balance | Balance | Balance | Balance |
| (2) Ingredient (C) Pentaerythritol distearate (*1) | 0.5 | 1.0 | 2.0 | 3.5 | 5.0 | — | — | — | — |
| (3) Control for ingredient (C) Glycerol tri-(caprylate-caprate) | — | — | — | — | — | 0.5 | — | — | — |
| (4) Control for ingredient (C) Di-(phytostearyl/octyldodecyl-N-lauroyl-L-glutamate) (*2) | — | — | — | — | — | — | 1.0 | — | 1.0 |
| (5) Control for ingredient (C) Pentaerythrityl tetra-(behenate/benzoate/ethylhexanoate) (*3) | — | — | — | — | — | 0.5 | — | 1.0 | 1.0 |
| (6) Ingredient (D) Microgel of Synthetic example 1 | — | — | — | — | — | — | 0.5 | 1.0 | 0.5 |
| (7) Control for ingredient (D) Carbomer | 0.1 | — | — | — | — | 0.2 | — | — | — |
| (8) Control for ingredient (D) Xanthan gum | — | 0.1 | — | — | — | — | — | — | — |
| (9) Control for ingredient (D) (Sodium acrylate/sodium acryloyldimethyltaurate) copolymer (*4) | — | — | 0.3 | — | — | — | — | — | — |
| (10) Control for ingredient (D) Ammonium polyacrylate (*5) | — | — | — | 0.5 | — | — | — | — | — |
| (11) Control for ingredient (D) Polyacrylamide (*6) | — | — | — | — | 1.0 | — | — | — | — |
| (12) Polyoxyethylene hydrogenated castor oil (60 mole ethylene oxide adduct) | 0.2 | 0.2 | 0.2 | 0.2 | 0.2 | 0.2 | 0.2 | 0.2 | 0.2 |
| (13) Dimethyl silicone 6 mPa · s | 1.0 | 1.0 | 1.0 | 1.0 | 1.0 | 1.0 | 1.0 | 1.0 | 1.0 |
| (14) Cetyl ethylhexanoate | 1.0 | 1.0 | 1.0 | 1.0 | 1.0 | 1.0 | 1.0 | 1.0 | 1.0 |
| (15) Squalane | 1.0 | 1.0 | 1.0 | 1.0 | 1.0 | 1.0 | 1.0 | 1.0 | 1.0 |
| (16) Citric acid | 0.02 | 0.02 | 0.02 | 0.02 | 0.02 | 0.02 | 0.02 | 0.02 | 0.02 |

TABLE 4-continued

| Ingredient name | Comparative example | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| (17) Sodium citrate | 0.08 | 0.08 | 0.08 | 0.08 | 0.08 | 0.08 | 0.08 | 0.08 | 0.08 |
| (18) Phenoxyethanol | 0.5 | 0.5 | 0.5 | 0.5 | 0.5 | 0.5 | 0.5 | 0.5 | 0.5 |
| (19) Ethanol | 3.0 | 3.0 | 3.0 | 3.0 | 3.0 | 3.0 | 3.0 | 3.0 | 3.0 |
| (20) Perfume | 0.1 | 0.1 | 0.1 | 0.1 | 0.1 | 0.1 | 0.1 | 0.1 | 0.1 |
| (21) Potassium hydroxide | Appropriate amount | — | — | — | — | Appropriate amount | — | — | — |
| Spreadability on the skin | ○ | Δ | ○ | X | ○ | ○ | Δ | Δ | ○ |
| Absorption into the skin | Δ | X | ○ | Δ | ○ | Δ | Δ | Δ | ○ |
| Stickiness | ○ | X | Δ | Δ | X | Δ | Δ | Δ | X |
| Dewy freshness | Δ | X | Δ | Δ | X | ○ | Δ | Δ | X |
| Permeating sensation | Δ | X | Δ | Δ | X | X | X | Δ | X |
| Emollient sensation | Δ | ○ | ○ | ○ | ○ | ○ | ○ | ○ | ◎ |
| Taut sensation | X | Δ | Δ | Δ | ○ | X | Δ | ○ | ○ |

(*1) Product name: Cutina PES from BASF
(*2) Product name: Eldew PS-203 from Ajinomoto Healthy Supply
(*3) Product name: Eldew PS-304 from Ajinomoto Healthy Supply
(*4) Product name: SIMULGEL EG from SEPIC
(*5) Product name: SIMULGEL A from SEPIC
(*6) Product name: SEPIGEL 305 from SEPIC Examples of Table 3 and Comparative examples of Table 4 indicate that the moisture retaining essences of Examples 2-1 through 2-9 have a superior texture in all the evaluation items.

INDUSTRIAL APPLICATIONS

The water-based skin cosmetic of the present invention or oil-in-water emulsified skin cosmetic of the present invention manifests good spreadability on and absorption into the skin, is free of stickiness, and excellent in terms of texture such as dewy freshness, a permeating sensation, emollient sensation, and taut sensation.

Therefore it can be used preferably for gel or cream-like products such as anti-aging essences, whitening essences, anti-aging creams, and whitening creams.

The invention claimed is:

1. A water-based cosmetic or water-based cream, comprising the following ingredients (A), (B), (C), and (D):
   (A) bis-PEG-18 methyl ether dimethyl silane;
   (B) a thickener composed of microgel obtained by using a composition that has an organic solvent or oil component as the dispersion medium and water as the dispersion phase, dissolving a water-soluble ethylenically unsaturated monomer in the dispersion phase, and radically polymerizing it in the dispersion phase, wherein said microgel is obtained by radically polymerizing dimethylacrylamide and 2-acrylamido-2-methylpropane sulfonic acid under the conditions in which a single phase microemulsion or fine W/O emulsion is formed by using a surfactant;
   (C) water; and
   (D) ethanol;
   wherein:
      the content of said ingredient (A), bis-PEG-18 methyl ether dimethyl silane, is 1.0-10.0 wt % relative to the total amount of the water-based cosmetic or water-based cream;
      the content of said ingredient (B), the thickener composed of the microgel, is 0.1-2.0 wt % relative to the total amount of the water-based cosmetic or water-based cream; and
      the content of said ingredient (C), water, is 74.8-85.2 wt % relative to the total amount of the water-based cosmetic or water-based cream.

2. The water-based cosmetic or water-based cream according to claim 1, wherein:
   the content of said ingredient (A), bis-PEG-18 methyl ether dimethyl silane, is 5.0-10.0 wt % relative to the total amount of the water-based cosmetic or water-based cream;
   the content of said ingredient (B), the thickener composed of the microgel, is 0.5-2.0 wt % relative to the total amount of the water-based cosmetic or water-based cream; and
   the content of said ingredient (C), water, is 74.8-80.8 wt % relative to the total amount of the water-based cosmetic or water-based cream.

* * * * *